United States Patent
Hong et al.

(10) Patent No.: US 9,963,527 B2
(45) Date of Patent: May 8, 2018

(54) TRANSITION METAL COMPOUND, CATALYST COMPOSITION COMPRISING THE SAME, AND METHOD OF PREPARING POLYOLEFIN

(71) Applicant: LG CHEM, LTD., Seoul (KR)

(72) Inventors: Bog Ki Hong, Daejeon (KR); Yong Ho Lee, Daejeon (KR); Chang Woan Han, Daejeon (KR); Yi Young Choi, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 15/314,303

(22) PCT Filed: Jun. 5, 2015

(86) PCT No.: PCT/KR2015/005658
§ 371 (c)(1),
(2) Date: Nov. 28, 2016

(87) PCT Pub. No.: WO2015/194777
PCT Pub. Date: Dec. 23, 2015

(65) Prior Publication Data
US 2017/0198074 A1 Jul. 13, 2017

(30) Foreign Application Priority Data
Jun. 18, 2014 (KR) .................. 10-2014-0074371

(51) Int. Cl.
*C07F 17/00* (2006.01)
*C08F 4/6592* (2006.01)
*C08F 210/16* (2006.01)
*C07F 7/08* (2006.01)
*C08F 4/659* (2006.01)

(52) U.S. Cl.
CPC ............ *C08F 210/16* (2013.01); *C07F 7/082* (2013.01); *C07F 17/00* (2013.01); *C08F 4/65908* (2013.01); *C08F 4/65912* (2013.01); *C08F 4/65927* (2013.01)

(58) Field of Classification Search
CPC .. C08F 4/65927; C08F 4/65912; C08F 10/00; C08F 210/16
See application file for complete search history.

(56) References Cited

U.S. PATENT DOCUMENTS

| | | |
|---|---|---|
| 5,064,802 A | 11/1991 | Stevens et al. |
| 8,124,557 B2 | 2/2012 | Lee et al. |
| 2007/0179044 A1 | 8/2007 | Yang et al. |
| 2009/0163688 A1 | 6/2009 | Marin et al. |
| 2012/0123078 A1 | 5/2012 | Lee et al. |
| 2012/0196985 A1 | 8/2012 | Lee et al. |
| 2013/0296519 A1 | 11/2013 | Lee et al. |

FOREIGN PATENT DOCUMENTS

| | | |
|---|---|---|
| EP | 0604908 A2 | 7/1994 |
| JP | 6256369 A | 9/1994 |
| KR | 10-2001-0043881 A | 5/2001 |
| KR | 10-2008-0100439 A | 11/2008 |
| KR | 10-2009-0035000 A | 4/2009 |
| KR | 10-2011-0013286 A | 2/2011 |
| KR | 10-2012-0087100 A | 8/2012 |
| KR | 10-2012-0087706 A | 8/2012 |
| KR | 10-2012-0087847 A | 8/2012 |
| KR | 101265891 B1 | 5/2013 |
| KR | 10-2015-0068084 A | 6/2015 |
| WO | 1999/62967 A2 | 12/1999 |

OTHER PUBLICATIONS

"Polymerization of Ethylene with Metallocene/Methylaluminoxane Catalyst Supported on Polysiloxane Micro Gels and Silica"; Journal of Organometallic Chemistry, 1998, vol. 568, pp. 263-269.

*Primary Examiner* — Caixia Lu
(74) *Attorney, Agent, or Firm* — Dentons US LLP

(57) ABSTRACT

The present invention relates to a novel transition metal compound, a catalyst composition comprising the transition metal compound, and a method of preparing polyolefin using the catalyst composition.

21 Claims, No Drawings

TRANSITION METAL COMPOUND, CATALYST COMPOSITION COMPRISING THE SAME, AND METHOD OF PREPARING POLYOLEFIN

CROSS-REFERENCE TO RELATED APPLICATION

This application is a National Stage Entry of International Application No. PCT/KR2015/005658, filed Jun. 5, 2015, and claims the benefit of and priority to Korean Application No. 10-2014-0074371, filed on Jun. 18, 2014, all of which are hereby incorporated by reference in their entirety for all purposes as if fully set forth herein.

TECHNICAL FIELD OF THE INVENTION

The present disclosure relates to a transition metal compound, a catalyst composition comprising the transition metal compound, and a method of preparing polyolefin. More specifically, the present disclosure relates to a transition metal compound with a novel chemical structure, and a transition metal catalyst composition and a method of preparing polyolefin by which polyolefin with high selectivity and reaction activity may be synthesized more easily and stably, and the content of alpha-olefins may be increased in the finally synthesized polyolefin.

BACKGROUND OF THE INVENTION

Dow Company presented [Me$_2$Si(Me$_4$C$_5$)NtBu]TiCl$_2$ (Constrained-Geometry Catalyst, hereinafter abbreviated as CGC) in the early 1990's (U.S. Pat. No. 5,064,802). Compared to the previously known metallocene catalysts, the advantages of CGC in the copolymerization reaction of ethylene and alpha-olefin can be summarized as follows: (1) it exhibits high activity even at high polymerization temperature, and simultaneously, produces high molecular weight polymer, and (2) it also has very excellent copolymerizability with alpha-olefins having large steric hindrance such as 1-hexene and 1-octene. In addition, as various properties of CGC in polymerization reactions have been gradually known, there have been vigorous attempts in academic and industrial fields to synthesize derivatives thereof and use them as polymerization catalysts.

A Group 4 metallocene compound having one or two cyclopentadienyl groups as ligand may be activated with methylaluminoxane or a boron compound to be used as a catalyst of olefin polymerization. Such catalyst exhibits unique properties which may not be realized by Ziegler-Natta catalysts of the prior art.

Specifically, a polymer obtained using the catalyst has narrow molecular weight distribution and better reactivity to second monomers such as alpha-olefin or cyclic olefin, and the distribution of the second monomers of the polymer is uniform. And, when alpha olefin is polymerized, stereoselectivity of the polymer may be controlled by changing substituents of the cyclopentadienyl ligand in the metallocene catalyst. In addition, when ethylene is copolymerized with other olefins, the degree of copolymerization, molecular weight, and the distribution of second monomers and the like may be easily controlled by changing substituents of the cyclpentadienyl ligand in the metallocene catalyst.

Meanwhile, since metallocene catalysts are expensive compared to Ziegler-Natta catalysts of the prior art, they may have economical value when they have good activity. If reactivity to second monomers is good, polymer including many second monomers may be obtained even with a small amount of second monomers introduced.

According to the results of studies on various catalysts by many researchers, it was proved that bridged catalysts generally have good reactivity to second monomers. Bridged catalysts which have been studied may be classified into three kinds according to the shape of the bridge. The first one is a catalyst wherein two cyclopentadienyl ligands are connected by an alkylene dibridge by the reaction of electrophile such as alkyl halide with indene or fluorene and the like, the second one is a silicon-bridged catalyst connected by —SiR$_2$—, and the third one is a methylene-bridged catalyst obtained from the reaction of fulvene with indene or fluorene and the like.

However, among these attempts, a few catalysts are practically applied in commercial process, and there has been continuous demand for the preparation of catalysts exhibiting more improved polymerization performance.

DETAILED DESCRIPTION OF THE INVENTION

It is an object of the invention to provide a transition metal compound having a novel chemical structure that can be used as a catalyst for the synthesis of polyolefin.

It is another object of the invention to provide a catalyst composition that can more easily and stably synthesize polyolefin with high selectivity and reaction activity, and can increase the content of alpha-olefins in the finally synthesized polyolefin.

It is still another object of the invention to provide a method of preparing polyolefin using the catalyst composition comprising the transition metal compound.

TECHNICAL SOLUTIONS

A transition metal compound represented by the following Chemical Formula 1 is provided herein:

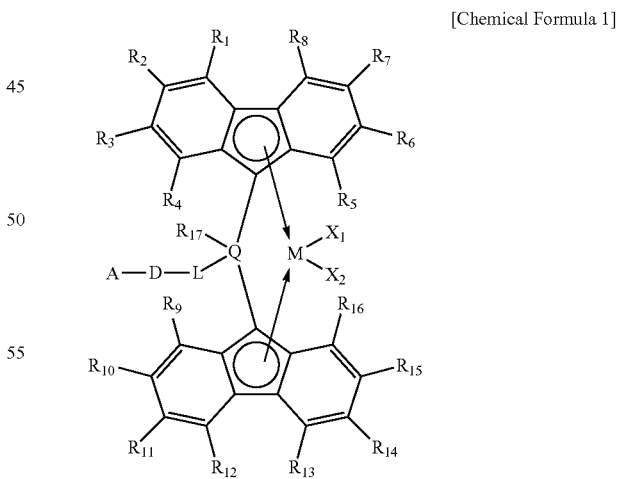

[Chemical Formula 1]

in the Chemical Formula 1,
Q is a Group 14 atom,
each of R$_5$, R$_6$, R$_7$, R$_8$, R$_{13}$, R$_{14}$, R$_{15}$ and R$_{16}$ is hydrogen, halogen, a C$_{1-20}$ linear or branched alkyl group, a C$_{2-20}$ linear or branched alkenyl group, a C$_{6-20}$ aryl group, or a C$_{7-20}$ alkylaryl group, at least one of $R_5$, $R_6$, $R_7$ and $R_8$ is a functional group of the following Chemical Formula 2, and at least one of $R_{13}$, $R_{14}$, $R_{15}$ and $R_{16}$ is a functional group of the following Chemical Formula 2, $R_1$, $R_2$, $R_3$, $R_4$, $R_9$, $R_{10}$, $R_{11}$ and $R_{12}$ are identical to or different from each other, and are each independently, hydrogen, halogen, a $C_{1-20}$ linear or branched alkyl group, a $C_{2-20}$ linear or branched alkenyl group, a $C_{6-20}$ aryl group, or a $C_{7-20}$ alkylaryl group, $R_{17}$ is a $C_{1-10}$ linear or branched alkyl group, a $C_{2-10}$ linear or branched alkenyl group, a $C_{6-10}$ aryl group, a $C_{7-10}$ alkylaryl group, or a $C_{7-10}$ arylalkyl group, L is a $C_{1-10}$ linear or branched alkylene group, D is —O—, —S—, —N(R)— or —Si(R)(R')—, wherein R and R are identical to or different from each other, and are each independently, hydrogen, halogen, a $C_{1-20}$ linear or branched alkyl group, a $C_{2-20}$ linear or branched alkenyl group, or a $C_{6-20}$ aryl group, A is hydrogen, halogen, a $C_{1-20}$ linear or branched alkyl group, a $C_{2-20}$ linear or branched alkenyl group, a $C_{6-20}$ aryl group, a $C_{7-20}$ alkylaryl group, a $C_{7-20}$ arylalkyl group, a $C_{1-20}$ alkoxy group, a $C_{2-20}$ alkoxyalkyl group, a $C_{2-20}$ heterocycloalkyl group, or a $C_{5-20}$ heteroaryl group, M is a Group 4 transition metal, $X_1$ and $X_2$ are identical to or different from each other, and are each independently, halogen, a $C_{1-20}$ alkyl group, a $C_{2-20}$ alkenyl group, a $C_{6-20}$ aryl group, a nitro group, an amino group, a $C_{1-20}$ alkylsilyl group, a $C_{1-20}$ alkoxy group, or a $C_{1-20}$ sulfonate group, and in the above Chemical Formula, → denotes a coordinate bond, -$E_1$-$G_1$      [Chemical Formula 2]

in the Chemical Formula 2, $E_1$ is a $C_{1-10}$ linear or branched alkylene group, and $G_1$ is a $C_{6-20}$ aryl group, a $C_{4-20}$ cycloalkyl group, or a $C_{2-20}$ alkoxyalkyl group.

And, a catalyst composition comprising the transition metal compound is provided herein.

And, a method of preparing polyolefin comprising the step of polymerizing olefin monomers in the presence of a catalyst composition comprising the transition metal compound is provided herein.

Hereinafter, a transition metal compound, a catalyst composition comprising the same, and a method of preparing polyolefin using the same according to specific embodiments of the invention will be explained in detail.

As used herein, alkyl means a monovalent functional group derived from alkane, alkenyl means a monovalent functional group derived from alkene, and aryl means a monovalent functional group derived from arene.

And, alkylene means a divalent functional group derived from alkane, alkenylene means a divalent functional group derived from alkene, and arylene means a divalent functional group derived from arene.

Unless otherwise described herein, all functional groups may include substituted and unsubstituted forms, examples of the substituents are not specifically limited, and various organic functional groups, inorganic functional groups or organic-inorganic complex functional groups commonly widely used can be used.

According to one embodiment of the invention, a transition metal compound represented by the above Chemical Formula 1 is provided.

The present inventors newly synthesized a transition metal compound of the Chemical Formula 1, confirmed through experiments that due to the electronic and steric structure of the transition metal compound of the Chemical Formula 1, ethylene/alpha-olefin copolymer may be more easily and stably synthesized from olefin monomers with high selectivity and reaction activity in the synthesis reaction of polyolefin, and that the content of alpha-olefins in the finally synthesized polyolefin may be increased, and completed the invention.

Particularly, in the transition metal compound of the Chemical Formula 1, a part where a transition metal M is located, due to the electronic and steric structure, can react alpha-olefins with high efficiency and selectivity in the reaction of ethylene monomers and alpha-olefins. Thus, by using the transition metal compound of the Chemical Formula 1, the copolymerizability of alpha-olefins in the finally synthesized polyolefin may be improved.

More specifically, in the Chemical Formula 1, Q is a Group 14 atom, and specific examples thereof may include silicon (Si) or germanium (Ge), preferably silicon.

In the Chemical Formula 1, each of $R_5$, $R_6$, $R_7$, $R_8$, $R_{13}$, $R_{14}$, $R_{15}$ and $R_{16}$ may be hydrogen, halogen, a $C_{1-20}$ linear or branched alkyl group, a $C_{2-20}$ linear or branched alkenyl group, a $C_{6-20}$ aryl group, or a $C_{7-20}$ alkylaryl group. The $C_{1-20}$ linear or branched alkyl group may include a methyl group, an ethyl group, a propyl group, an isopropyl group, an n-butyl group, a tert-butyl group, a pentyl group, a hexyl group, a heptyl group, an octyl group, and the like, the $C_{2-20}$ linear or branched alkenyl group may include an allyl group, an ethenyl group, a propenyl group, a butenyl group, a pentenyl group, and the like, and the $C_{6-20}$ aryl group may include an aryl group of a single ring or a condensed ring, specifically, a phenyl group, a biphenyl group, a naphthyl group, a phenanthrenyl group, a fluorenyl group, and the like.

And, at least one of the $R_5$, $R_6$, $R_7$ and $R_8$ is a functional group of the Chemical Formula 2, and at least one of the $R_{13}$, $R_{14}$, $R_{15}$ and $R_{16}$ is a functional group of the Chemical Formula 2.

In the Chemical Formula 2, $E_1$ is a $C_{1-10}$ linear or branched alkylene group, and $G_1$ is a $C_{6-20}$ aryl group, a $C_{4-20}$ cycloalkyl group, or a $C_{2-20}$ alkoxyalkyl group. The $C_{6-20}$ aryl group may include an aryl group of a single ring or condensed ring, specifically, a phenyl group, a biphenyl group, a naphthyl group, a phenanthrenyl group, a fluorenyl group, and the like, the $C_{1-10}$ linear or branched alkylene group may be unsubstituted or substituted with a $C_{1-20}$ linear or branched alkyl group, a $C_{2-20}$ linear or branched alkenyl group, or a $C_{6-20}$ aryl group. The $C_{1-20}$ linear or branched alkyl group may include a methyl group, an ethyl group, a propyl group, an isopropyl group, an n-butyl group, a tert-butyl group, a pentyl group, a hexyl group, a heptyl group, an octyl group, and the like, and the $C_{2-20}$ linear or branched alkenyl group may include an allyl group, an ethenyl group, a propenyl group, a butenyl group, a pentenyl group, and the like.

And, in the Chemical Formula 2, $G_1$ may be a $C_{6-14}$ aryl group, a $C_{4-10}$ cycloalkyl group, or a $C_{2-15}$ alkoxyalkyl group. And, in the Chemical Formula 2, $G_1$ may be a $C_{6-10}$ aryl group or a $C_{5-6}$ cycloalkyl group, and specific examples thereof may include a phenyl group, a naphthyl group, a cyclopentyl group or a cyclohexyl group.

$E_1$ may be a $C_{1-4}$ linear or branched alkylene group.

That is, the functional group of the Chemical Formula 2 is a bulky and flexible functional group, and can bind to at least one position of $R_5$, $R_6$, $R_7$ and $R_8$, and at least one position of $R_{13}$, $R_{14}$, $R_{15}$ and $R_{16}$ of the transition metal compound of the Chemical Formula 1 to form a unique steric structure in the vicinity of the transition metal M.

In the transition metal compound of the Chemical Formula 1, M is a part where the reaction of ethylene monomers and alpha-olefins is progressed, and as a bulky and flexible functional group of the Chemical Formula 2 is located in the vicinity of the transition metal M, a bite angle of the transition metal M increases. And, solubility of the transition metal compound of the Chemical Formula 1 in a catalyst composition may increase. Thus, a synthesis reaction of polyolefin using the transition metal compound of the Chemical Formula 1 may exhibit high selectivity and reaction activity.

Meanwhile, in the Chemical Formula 1, each of $R_5$, $R_7$, $R_8$, $R_{13}$, $R_{14}$ and $R_{16}$ may be hydrogen, halogen, a $C_{1-3}$ linear or branched alkyl group, and each of $R_6$ and $R_{15}$ may be a functional group of the following Chemical Formula 3.

-$E_2$-$G_2$ [Chemical Formula 3]

in the Chemical Formula 3, $G_2$ is a $C_{6-10}$ aryl group or a $C_{5-6}$ cycloalkyl group, and specific examples thereof may include a phenyl group, a naphthyl group, a cyclopentyl group or a cyclohexyl group. $E_2$ is a $C_{1-4}$ linear or branched alkylene group, and specific examples thereof may include a methylene, an ethylene, a propylene or a butylene group.

In the Chemical Formula 1, $R_1$, $R_2$, $R_3$, $R_4$, $R_9$, $R_{10}$, $R_{11}$ and $R_{12}$ are identical to or different from each other, and are each independently, hydrogen, halogen, a $C_{1-20}$ linear or branched alkyl group, a $C_{2-20}$ linear or branched alkenyl group, a $C_{6-20}$ aryl group, a $C_{7-20}$ alkylaryl group. The $C_{1-20}$ linear or branched alkyl group may include a methyl group, an ethyl group, a propyl group, an isopropyl group, an n-butyl group, a tert-butyl group, a pentyl group, a hexyl group, a heptyl group, an octyl group, and the like, the $C_{2-20}$ linear or branched alkenyl group may include an allyl group, an ethenyl group, a propenyl group, a butenyl group, a pentenyl group, and the like, the $C_{6-20}$ aryl group may include an aryl group of a single ring or a condensed ring, specifically, a phenyl group, a biphenyl group, a naphthyl group, a phenanthrenyl group, a fluorenyl group, and the like.

And, in the Chemical Formula 1, each of $R_1$, $R_2$, $R_3$, $R_4$, $R_9$, $R_{10}$, $R_{11}$ and $R_{12}$ may be independently hydrogen, halogen or a $C_{1-8}$ linear or branched alkyl group. Specific examples of the $C_{1-8}$ linear or branched alkyl group may include hydrogen, a methyl group, an ethyl group, a propyl group, an isopropyl group, an n-butyl group, a tert-butyl group, a pentyl group, a hexyl group, a heptyl group, or an octyl group, and the like.

In the Chemical Formula 1, $R_{17}$ is a $C_{1-10}$ linear or branched alkyl group, a $C_{2-20}$ linear or branched alkenyl group, a $C_{6-10}$ aryl group, a $C_{7-10}$ alkylaryl group, or a $C_{7-10}$ arylakyl group.

And, $R_{17}$ may be a $C_{1-3}$ alkyl group, and specific examples of the $C_{1-3}$ alkyl group may include a methyl group, an ethyl group, a propyl group, and the like.

In the Chemical Formula 1, L may be a $C_{1-10}$ linear or branched alkylene group, and the $C_{1-10}$ linear or branched alkylene group may be unsubstituted or substituted with a $C_{1-20}$ linear or branched alkyl group, a $C_{2-20}$ linear or branched alkenyl group, or a $C_{6-20}$ aryl group. The $C_{1-20}$ linear or branched alkyl group may include a methyl group, an ethyl group, a propyl group, an isopropyl group, an n-butyl group, a tert-butyl group, a pentyl group, a hexyl group, a heptyl group, an octyl group, and the like, the $C_{2-20}$ linear or branched alkenyl group may include an allyl group, an ethenyl group, a propenyl group, a butenyl group, a pentenyl group, and the like, the $C_{6-20}$ aryl group may include an aryl group of a single ring or a condensed ring, specifically, a phenyl group, a biphenyl group, a naphthyl group, a phenanthrenyl group, a fluorenyl group, and the like.

And, L may be a $C_{3-8}$ linear or branched alkylene group. Specific examples of the $C_{3-8}$ linear or branched alkylene group may include propylene, butylenes, pentylene, hexylene, and the like.

In the Chemical Formula 1, D is —O—, —S—, —N(R)— or —Si(R)(R')—, and R and R' are identical to or different from each other, and are each independently, hydrogen, halogen, a $C_{1-20}$ linear or branched alkyl group, a $C_{2-20}$ linear or branched alkenyl group, a $C_{6-20}$ aryl group, wherein the $C_{1-20}$ linear or branched alkyl group may include a methyl group, an ethyl group, a propyl group, an isopropyl group, an n-butyl group, a tert-butyl group, a pentyl group, a hexyl group, a heptyl group, an octyl group, and the like, the $C_{2-20}$ linear or branched alkenyl group may include an allyl group, an ethenyl group, a propenyl group, a butenyl group, a pentenyl group, and the like, and the $C_{6-20}$ aryl group may include an aryl group of a single ring or a condensed ring, specifically, a phenyl group, a biphenyl group, a naphthyl group, a phenanthrenyl group, a fluorenyl group, and the like.

Alternatively, D may be —O— or —S—.

In the Chemical Formula 1, A is hydrogen, halogen, a $C_{1-20}$ linear or branched alkyl group, a $C_{2-20}$ linear or branched alkenyl group, a $C_{6-20}$ aryl group, a $C_{7-20}$ alkylaryl group, a $C_{7-20}$ arylalkyl group, a $C_{1-20}$ alkoxy group, a $C_{2-20}$ alkoxyalkyl group, a $C_{2-20}$ heterocycloalkyl group, or a $C_{5-20}$ heteroaryl group. The $C_{5-20}$ heteroaryl group may include a heteroaryl group of a single ring or a condensed ring, and specifically, a carbazolyl group, a pyridyl group, a quinoline group, an isoquinoline group, a thiophenyl group, a furanyl group, an imidazole group, an oxazolyl group, a thiazolyl group, a triazine group, a tetrahydropyranyl group, a tetrahydrofuranyl group, and the like. Examples of the $C_{1-20}$ alkoxy group may include a methoxy group, an ethoxy group, a phenyloxy group, a cyclohexyloxy group, and the like. Specific examples of A may include a $C_{3-5}$ linear or branched alkyl group, specifically, a propyl group, an isopropyl group, an n-butyl group, a tert-butyl group.

And, A may be a $C_{3-5}$ linear or branched alkyl group. Specific examples of the $C_{3-5}$ linear or branched alkyl group may include a propyl group, an isopropyl group, an n-butyl group, a tert-butyl group, a pentyl group.

In the Chemical Formula 1, M is a Group 4 transition metal, for example, titanium, zirconium, or hafnium.

In the Chemical Formula 1, $X_1$ and $X_2$ are identical to or different from each other, and are each independently, halogen, a $C_{1-20}$ linear or branched alkyl group, a $C_{2-20}$ linear or branched alkenyl group, a $C_{6-20}$ aryl group, a nitro group, an amino group, a $C_{1-20}$ alkylsilyl group, a $C_{1-20}$ alkoxy group, or a $C_{1-20}$ sulfonate group. Specific examples of $X_1$ and $X_2$ may include a $C_{1-4}$ linear or branched alkyl group, or a $C_{1-4}$ alkoxy group.

Meanwhile, specific examples of the transition metal compound of the Chemical Formula 1 may include compounds of the following Chemical Formula 4. That is, the transition metal compound may include compounds of the following Chemical Formula 4.

[Chemical Formula 4]

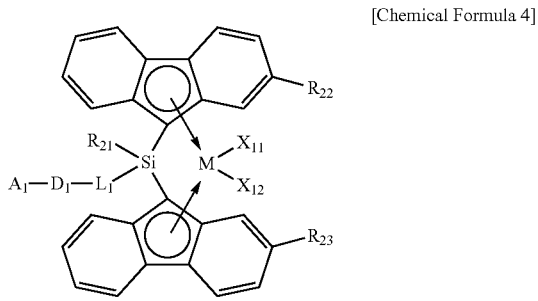

In the Chemical Formula 4, M may be titanium, zirconium or hafnium.

In the Chemical Formula 4, each of $X_{11}$ and $X_{12}$ is halogen, a $C_{1-4}$ linear or branched alkyl group, or a $C_{1-4}$ alkoxy group, and specific examples of $X_{11}$ and $X_{12}$ may include halogen or a methyl group.

In the Chemical Formula 4, $R_{21}$ is a $C_{1-3}$ alkyl group, and specific examples thereof may include a methyl group, an ethyl group, or a propyl group.

In the Chemical Formula 4, $L_1$ is a $C_{3-8}$ linear or branched alkylene group, and specific examples thereof may include propylene, butylene, pentylene, or hexylene.

In the Chemical Formula 4, $D_1$ may be —O— or —S—, more preferably —O—.

In the Chemical Formula 4, $A_1$ is a $C_{3-5}$ linear or branched alkyl group, more specifically, a propyl group, an isopropyl group, an n-butyl group, a tert-butyl group, or a pentyl group.

In the Chemical Formula 4, each of $R_{22}$ and $R_{23}$ is a functional group of the following Chemical Formula 3, -$E_2$-$G_2$    [Chemical Formula 3]

In the Chemical Formula 3, $G_2$ is a $C_{6-10}$ aryl group or a $C_{5-6}$ cycloalkyl group, and specific examples thereof may include a phenyl group, a naphthyl group, a cyclopentyl group or a cyclohexyl group. $E_2$ is a $C_{1-4}$ linear or branched alkylene group, and specific examples thereof may include methylene, ethylene, propylene, or butylene.

More specifically, the transition metal compound may include compounds of the following Chemical Formula 5 and Chemical Formula 6.

[Chemical Formula 5]

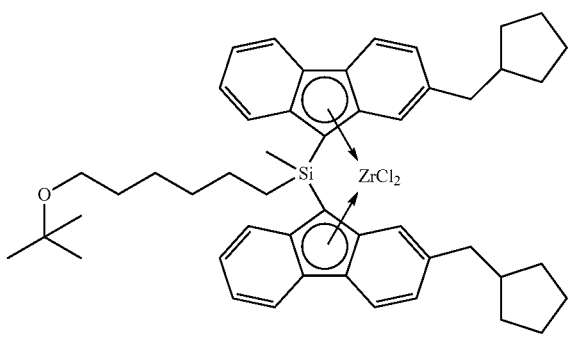

[Chemical Formula 6]

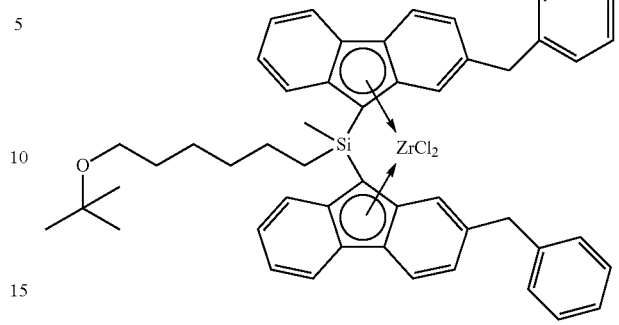

Meanwhile, according to another embodiment of the invention, a catalyst composition comprising a transition metal compound represented by the Chemical Formula 1 is provided.

The transition metal catalyst composition may be used for the synthesis reaction of ethylene/alpha-olefin copolymer. When the transition metal compound of the Chemical Formula 1 is used, it may exhibit high reactivity in the synthesis reaction of ethylene/alpha-olefin copolymer, and may easily control the properties such as chemical structure, molecular weight distribution, processibility, or mechanical properties of the synthesized ethylene/alpha-olefin copolymer.

Particularly, a catalyst composition comprising the transition metal compound of the Chemical Formula 1 has relatively excellent stability, and may exhibit efficient steric hindrance effect with a non-complex coordination structure to realize excellent catalytic activity and variously modify selectivity to copolymer. Thus, by using the transition metal catalyst composition, polyolefin having various properties may be provided.

Meanwhile, the transition metal catalyst composition may further comprise a cocatalyst. Specifically, the cocatalyst may include compounds of the following Chemical Formulae 11 to 13, or a mixture of two or more kinds thereof.

[L-H]$^+$[Z(E)$_4$]$^-$ or [L]$^+$[Z(E)$_4$]$^-$    [Chemical Formula 11]

In the Chemical Formula 11, L is neutral or cationic Lewis base, [L-H]+ or [L]$^+$ is Bronsted acid, H is a hydrogen atom, Z is a Group 13 atom (preferably, boron or aluminum in the oxidation state of +3), and Es may be identical to or different from each other, and are each independently, halogen having hydrogen valence of one or more, a $C_{1-20}$ hydrocarbyl, a $C_{6-20}$ aryl group or a $C_{1-20}$ alkyl group unsubstituted or substituted with an alkoxy or phenoxy functional group. The 'hydrocarbyl' is a monovalent functional group obtained by removing hydrogen atom from hydrocarbon, and may include ethyl, phenyl, and the like.

D(R$_{31}$)$_3$    [Chemical Formula 12]

In the Chemical Formula 12, D is aluminum or boron, $R_{31}$s may be identical to or different from each other, and are each independently, a $C_{1-20}$ hydrocarbon group; or a $C_{1-20}$ hydrocarbon group substituted with halogen.

[Chemical Formula 13]

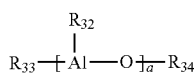

In the Chemical Formula 13, $R_{32}$, $R_{33}$ and $R_{34}$ may be identical to or different from each other, and are each independently, hydrogen; a halogen group; a $C_{1-20}$ aliphatic hydrocarbon group; or a $C_{1-20}$ aliphatic hydrocarbon group substituted with halogen, and a is an integer of 2 or more.

The compound of the Chemical Formula 11 may function to activate the transition metal compound of the Chemical Formula 1, and may comprise non-coordination-bonding anion that is compatible with bronsted acid cation. Preferably, the anion includes a mono coordinate complex having a relatively large size and including metalloid. Particularly, compounds containing a single boron atom in the anion part are widely used. In this respect, salts containing an anion including a coordination complex containing a single boron atom are preferable.

In the transition metal catalyst composition, the mole number of the transition metal compound of the Chemical Formula 1: the mole number of the compounds of the Chemical Formula 11 may be 1:1 to 1:10, or 1:4 to 1:8. If the mole ratio is less than 1:1, the amount of the cocatalyst is relatively small, and activation of the metal compound may not be completely achieved, and thus, the activity of the transition metal catalyst may not be sufficient. If the mole ratio is greater than 1:10, the activity of the transition metal catalyst may increase. However, in this case, cocatalyst is used more than necessary, and thus, the production cost may largely increase.

Specific examples of the compounds of the Chemical Formula 11 may include triethylammonium tetra(phenyl) boron, tributylammonium tetra(phenyl)boron, trimethylammonium tetra(phenyl)boron, tripropylammonium tetra(phenyl)boron, trimethylammonium tetra(p-tolyl) boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetra(pentafluorophenyl)boron, N,N-diethylanilidium tetra(phenyl)boron, N,N-diethylanilinium tetra(phenyl)boron, N,N-diethylanilinium tetra(pentafluorophenyl)boron, diethylammonium tetra(pentafluorophenyl) boron, triphenylphosphonium tetra(phenyl)boron, trimethylphosphonium tetra(phenyl)boron, triethylammonium tetra (phenyl)aluminum, tributylammonium tetra(phenyl) aluminum, trimethylammonium tetra(phenyl)aluminum, tripropylammonium tetra(phenyl)aluminum, trimethylammonium tetra(p-tolyl)aluminum, tripropylammonium tetra (p-tolyl)aluminum, triethylammonium tetra(o,p-dimethylphenyl)aluminum, tributylammonium tetra(p-trifluoromethylphenyl)aluminum, trimethylammonium tetra (p-trifluoromethylphenyl)aluminum, tributylammonium tetra(pentafluorophenyl)aluminum, N,N-diethylanilinium tetra(phenyl)aluminum, N,N-diethylanilinium tetra(phenyl) aluminum, N,N-diethylanilinium tetra(pentafluorophenyl) aluminum, diethylammonium tetra(pentafluorophenyl)aluminum, triphenylphosphonium tetra(phenyl)aluminum, trimethylphosphonium tetra(phenyl)aluminum, trimethylammonium tetra(phenyl)boron, tributylammonium tetra (phenyl)boron, trimethylammonium tetra(phenyl) boron, tripropylammonium tetra(phenyl) boron, trimethylammonium tetra(p-tollyl)boron, tripropylammonium tetra(p-tolyl) boron, triethylammonium tetra(o,p-dimethylphenyl)boron, trimethylammonium tetra(o,p-dimethylphenyl)boron, tributylammonium tetra(p-trifluoromethylphenyl) boron, trimethylammonium tetra(p-trifluoromethylphenyl) boron, tributylammonium tetra(pentafluorophenyl) boron, N,N-diethylanilinium tetra(phenyl) boron, N,N-diethylanilinium tetra(phenyl) boron, N,N-diethylanilinium tetra(pentafluorophenyl) boron, diethylammonium tetra(pentafluorophenyl) boron, triphenylphosphonium tetra(phenyl)boron, triphenylcarbonium tetra(p-trifluoromethylphenyl)boron, triphenylcarbonium tetra(pentafluorophenyl)boron, trityl tetra(pentafluorophenyl)boron, and the like, but are not limited thereto.

Meanwhile, the compound of the Chemical Formula 12 or 13 may function as a scavenger that removes impurities acting as a catalyst poison in the reactants.

In the transition metal catalyst composition, the mole number of the transition metal compound of the Chemical Formula 1: the mole number of the compound of the Chemical Formula 12 or 13 may be 1:1 to 1:8,000, or 1:10 to 1:5,000. If the mole ratio is less than 1:1, the effect resulting from the addition of a scavenger may be insignificant, and if it is greater than 1:5,000, excessive alkyl groups and the like that cannot participate in the reaction may inhibit a catalyst reaction and act as a catalyst poison, and thus, side-reactions may be progressed and excessive aluminum or boron may remain in the polymer.

Specific examples of the compound of the Chemical Formula 12 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron. In addition, preferably, trimethylaluminum, triethylaluminum or triisobutylaluminum may be used.

Specific examples of the compound of the Chemical Formula 13 may include methylaluminoxane, ethylaluminoxane, isobutylaluminoxane, butylaluminoxane, and the like. Preferably, methylaluminoxane may be used.

The transition metal catalyst composition may further comprise 50 to 1,000 parts by weight of organic solvents, based on 100 parts by weight of the transition metal compound of the Chemical Formula 1.

Although specific examples of the organic solvent are not limited, for example, it may include aliphatic hydrocarbon solvents such as pentane, hexane, heptane, nonane, decane and isomer thereof; aromatic hydrocarbon solvents such as toluene, xylene, benzene; or chlorine-substituted hydrocarbon solvents such as dichloromethane, chlorobenzene, and the like. The content of the organic solvent in the transition metal catalyst composition may be appropriately controlled according to the properties of the catalyst composition used and the applied conditions of polyolefin preparation process, and the like.

The transition metal catalyst composition may further comprise a carrier in which the active ingredient of the catalyst is fixed. The transition metal compound of the Chemical Formula 1 or the cocatalyst may be used while being fixed in the carrier, and the carrier is not specifically limited as long as it is known to be commonly used in a catalyst for the preparation of polyolefin, and for example, silica, alumina, magnesia or a mixture thereof may be used. And, the carrier may be dried at high temperature, and may commonly comprise oxide, carbonate, sulfate, nitrate components such as $Na_2O$, $K_2CO_3$, $BaSO_4$ and $Mg(NO_3)_2$, and the like.

Meanwhile, according to still another embodiment of the invention, a method of preparing polyolefin comprising the step of polymerizing olefin monomers in the presence of a catalyst composition comprising the transition metal compound of the Chemical Formula 1 is provided.

The olefin monomers used in the preparation method of polyolefin may include ethylene or alpha-olefin having a carbon number of 3 or more, or 3 to 80. Specific examples of the $C_{3-80}$ alpha-olefin may include propylene, 1-butene, 1-pentene, 4-methyl-1-pentene, 1-hexene, 1-heptene, 1-octene, 1-decene, 1-undecene, 1-dodecene, 1-tetradecen, 1-hexadecene, 1-eicosene, norbornene, norbonadiene, ethylidene norbordene, phenyl norbordene, vinyl norbordene, dicylcopentadiene, 1,4-butadiene, 1,5-pentadiene, 1,6-hexadiene, styrene, alpha-methylstyrene, divinylbenzene, 3-chloromethlystyrene, or mixtures thereof.

Although examples of the synthesized polyolefin are not specifically limited, for example, it may be olefin homopolymer, olefin copolymer or ethyhlene/alpha-olefin copolymer.

As explained, the transition metal catalyst composition of the above embodiment, due to the electronic and steric structure of the transition metal compound of the Chemical Formula 1, may react the alpha-olefins with high efficiency and high selectivity in the reaction of ethylene monomer and alpha-olefins. Thus, by using the transition metal compound of the Chemical Formula 1, copolymerizability of alpha-olefin in the finally synthesized polyolefin may be improved.

Although the polymerization reaction of olefin monomers may be progressed by a continuous solution polymerization process, a bulk polymerization process, a suspension polymerization process or an emulsion polymerization process, and the like, without limitations, for example, it may be progressed by a supported copolymerization reaction or a solution polymerization reaction carried out in a single reactor. The solution polymerization is carried out in a solution state by directly dissolving the transition metal catalyst composition in a solvent, and the supported polymerization is carried out in a slurry state by supporting the transition metal catalyst composition in the above explained carrier to prepare a supported catalyst, and then, introducing the supported catalyst in a solvent.

The polymerization reaction of olefin monomers may be carried out at a temperature of 45° C. to 200° C., or 60° C. to 100° C., for 0.3 hrs to 2.5 hrs, or 0.4 hrs to 1.3 hrs. And, it may be progressed at a pressure of 1 bar to 50 bar or 2 bar to 45 bar. Specifically, the solution polymerization may be progressed at a pressure of 1 bar to 5 bar and a temperature of 60° C. to 100° C. for 0.15 hrs to 1 hr, and the supported polymerization reaction may be progressed at a pressure of 1 bar to 50 bar and a temperature of 60° C. to 90° C. for 0.5 hrs to 2.5 hrs.

Although the reactors used in the polymerization reaction are not specifically limited, for example, a continuous stirred type reactor (CSTR) or a plug flow reactor (PFR) may be used. In the polymerization reaction, two or more reactors may be arranged in series or parallel, and the reactor may further comprise a separator for continuously separating solvents and non-reacted monomers from the reaction mixture.

The polyolefin may have a weight average molecular weight of 50,000 to 500,000, or 150,000 to 170,000 under solution polymerization condition, and it may have a weight average molecular weight of 100,000 to 1,000,000, or 400,000 to 500,000 under supported polymerization conditions.

Advantageous Effect of the Invention

According to the present disclosure, a transition metal compound that can more easily and stably synthesize polyolefin with high selectivity and reaction activity, and can increase the content of alpha-olefin in the synthesized polyolefin, a catalyst composition comprising the same and a method of preparing polyolefin may be provided.

DETAILED DESCRIPTION OF THE EMBODIMENTS

The present invention will be explained in detail in the following examples. However, these examples are presented only to illustrate the invention, and the scope of the invention is not limited thereto.

PREPARATION EXAMPLE 1

Preparation of a Transition Metal Compound (1) Preparation of a Ligand Compound

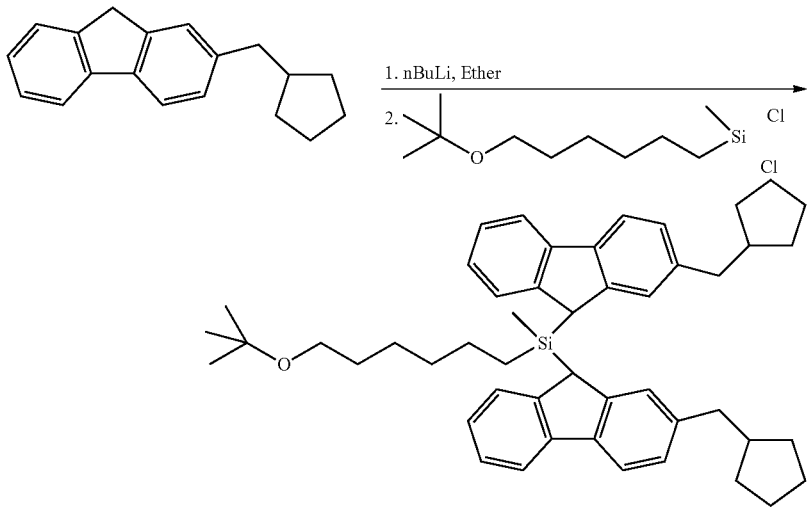

1 mole of a tert-Bu-O—$(CH_2)_6$MgCl solution, a Grignard reagent, was obtained by the reaction of a tert-Bu-O—$(CH_2)_6$ Cl compound and Mg(O) in a THF solvent. The prepared Grignard compound was added to a flask containing THF (2.0 ml) and a MeSiCl$_3$ compound (176.1 ml, 1.5 mol) of −30° C., and the solution was stirred at room temperature for 8 hours or more, and then, the filtered solution was vacuum dried to obtain a compound of tert-Bu-O—(CH$_2$)$_6$SiMeCl$_2$ (yield 92%).

In a dry ice/acetone bath of −20° C., 2-(cyclopentylmethyl)-9H-fluorene(CypenmeFlu)(3.33 g, 20 mmol) was dissolved in 50 ml of diethyl ether, 4.4 ml (11 mmol) of n-BuLi (2.5 M in Hexane) was slowly added, and the solution was stirred at room temperature for 6 hours to prepare a 2-(cyclopentylmethyl)-9H-fluoreny lithium solution. After the stirring was completed, the temperature of the reactor was cooled to −30° C., and the above prepared 2-(cyclopentylmethyl)-9H-fluoreny lithium solution was slowly added to a solution of tert-Bu-O—(CH$_2$)$_6$SiMeCl$_2$ (1.49 g, 5.5 mmol) in hexane (100 ml) at −30° C. for 1 hour. After stirring at room temperature for 8 hours or more, water was added to extract, followed by evaporation to obtain a compound of (6-(tert-butoxy)hexyl)bis(2-(cyclopentylmethyl)-9H-fluoren-9-yl)(methyl)silane (3.06 g, yield 88.1%). The structure of the ligand was confirmed through 1H-NMR.

1H NMR (500 MHz, CDCl$_3$): −0.32 (3H, d), 0.25-1.73 (35H, m), 2.09-2.14 (2H, dd), 2.64-2.71 (4H, m), 3.21-3.24 (2H, m), 4.04(1H, d), 4.10(1H, d), 7.16-7.84 (14H, m)

(2) Preparation of a Transition Metal Compound

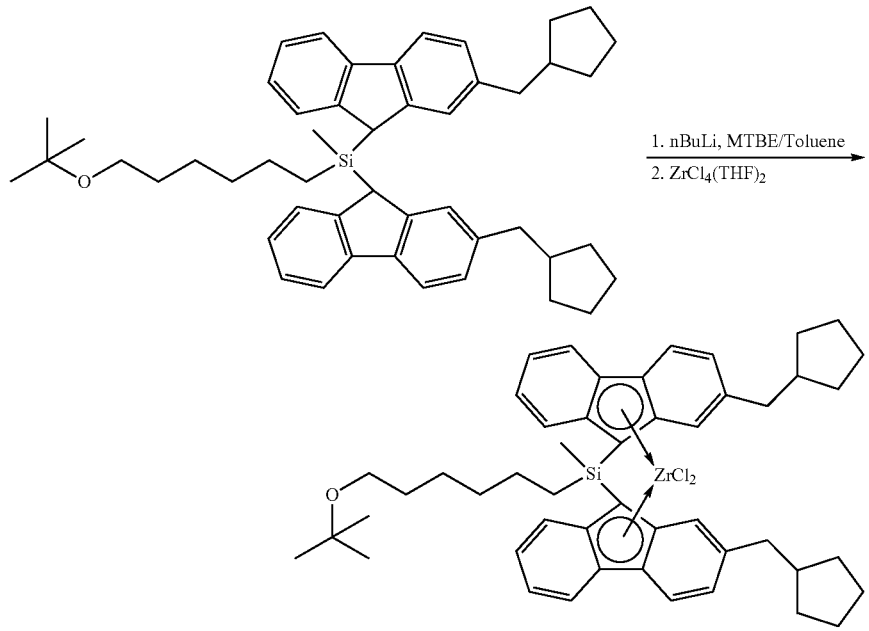

(6-(tert-butoxy)hexyl)bis(2-(cyclopentylmethyl)-9H-fluoren-9-yl)(methyl)silane(3.06 g, 4.4 mmol) was dissolved in 50 ml of toluene at −20° C., 2.1 ml of MTBE was added thereto, 3.9 ml of n-BuLi (2.5 M in Hexane) was slowly added to the solution, and the solution was reacted for 8 hours or more while raising the temperature to room temperature, and then, the above prepared slurry solution of dilithium salts was slowly added to a slurry solution of ZrCl$_4$(THF)$_2$ (1.66 g, 4.4 mmol)/toluene (100 ml) at −20° C., and the solution was further reacted at room temperature for 8 hours. The precipitate was filtered and washed with hexane several times to obtain a compound of (tert-Bu-O—(CH$_2$)$_6$)MeSi(9-C$_{19}$H$_{15}$)$_2$ZrCl$_2$ in the form of solid (1.25 g, yield 33.2%).

1H NMR (500 MHz, CDCl$_3$): 1.21-1.27 (12H, m), 1.59-1.89 (22H, m), 2.10-2.24 (6H, m), 2.49-2.72(4H, m), 3.46 (2H, t), 7.02-1.41 (14H, m)

PREPARATION EXAMPLE 2

Preparation of a Transition Metal Compound (1) Preparation of a Ligand Compound

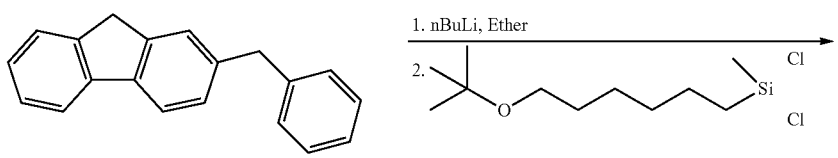

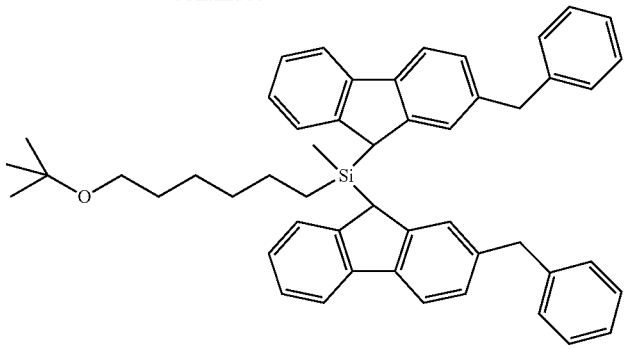

1 mole of a tert-Bu-O—(CH₂)₆MgCl solution, a Grignard reagent, was obtained by the reaction of a tert-Bu-O—(CH₂)₆Cl compound and Mg(O) in a THF solvent. The prepared Grignard compound was added to a flask containing THF (2.0 ml) and a MeSiCl₃ compound (176.1 ml, 1.5 mol) of −30° C., and the solution was stirred at room temperature for 8 hours or more, and then, the filtered solution was vacuum dried to obtain a compound of tert-Bu-O—(CH₂)₆SiMeCl₂ (yield 92%).

In a dry ice/acetone bath of −20° C., 2-(Benzyl)-9H-fluorene(BnFlu) (5.13 g, 20 mmol) was dissolved in 100 ml of diethyl ether, 9.2 ml (23 mmol) of n-BuLi (2.5 M in Hexane) was slowly added, and the solution was stirred at room temperature for 6 hours to prepare a 2-(benzyl)-9H-fluoreny lithium solution. After the stirring was completed, the temperature of the reactor was cooled to −30° C., and the above prepared 2-(benzyl)-9H-fluoreny lithium solution was slowly added to a solution of tert-Bu-O—(CH₂)₆SiMeCl₂ (2.71 g, 10 mmol) in hexane (50 ml) at −30° C. for 1 hour. After stirring at room temperature for 8 hours or more, water was added to extract, followed by evaporation to obtain a compound of 6-(tert-butoxy)hexyl)bis(2-(benzyl)-9H-fluoren-9-yl)(methyl)silane (4.96 g, yield 69.8%). The structure of the ligand was confirmed through 1H-NMR.

1H NMR (500 MHz, CDCl₃): (−0.49)-(−0.35) (3H, m), 0.10-1.31 (19H, m), 3.16-3.21 (2H, m), 3.79 (1H, s), 3.91-3.96(5H, m), 7.00-7.35 (24H, m)

(2) Preparation of a Transition Metal Compound

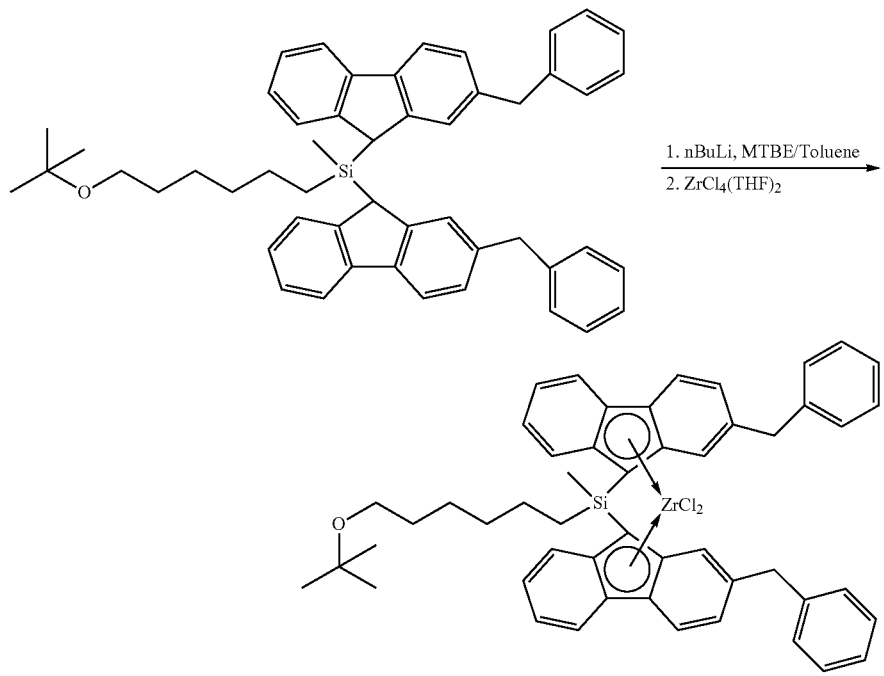

(6-(tert-butoxy)hexyl)bis(2-(benzyl)-9H-fluoren-9-yl)(methyl)silane(4.96 g, 7 mmol) was dissolved in 100 ml of toluene at −20° C., 3.3 ml (4.0 eq) of MTBE was added thereto, 6.1 ml (2.2 eq) of n-BuLi (2.5 M in Hexane) was slowly added to the solution, and the solution was reacted for 8 hours or more while raising the temperature to room temperature, and then, the above prepared slurry solution of dilithium salts was slowly added to a slurry solution of ZrCl₄(THF)₂ (2.63 g, 7 mmol)/toluene (100 ml) at −20° C., and the solution was further reacted at room temperature for 8 hours. The precipitate was filtered and washed with hexane several times to obtain a compound of (tert-Bu-O—(CH$_2$)$_6$)MeSi(9-C$_{20}$H$_{14}$)$_2$ZrCl$_2$ in the form of solid (3.58 g, yield 58.9%).

1H NMR (500 MHz, CDCl$_3$): 1.16-1.20 (9H, m), 1.34 (3H, s), 1.45-1.92 (10H, m), 3.36-3.38(2H, m), 3.86-3.96 (4H, m), 6.90-7.81 (24H, m)

PREPARATION EXAMPLE 3

Preparation of a Transition Metal Compound (1) Preparation of a Ligand Compound

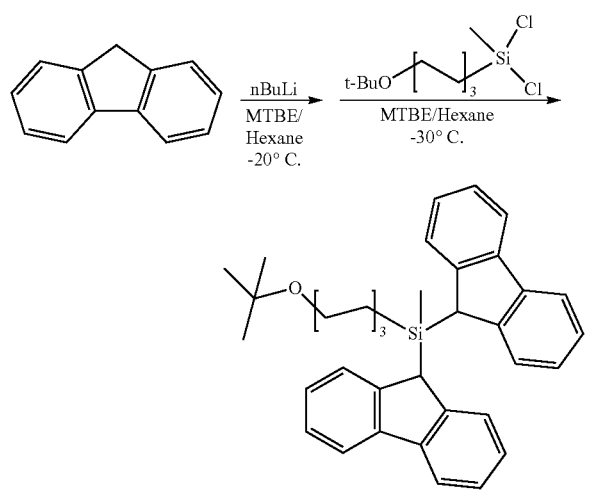

1 mole of a tert-Bu-O—(CH$_2$)$_6$MgCl solution, a Grignard reagent, was obtained by the reaction of a tert-Bu-O—(CH$_2$)$_6$ Cl compound and Mg(O) in a THF solvent. The prepared Grignard compound was added to a flask containing THF (2.0 ml) and a MeSiCl$_3$ compound (176.1 ml, 1.5 mol) of −30° C., and the solution was stirred at room temperature for 8 hours or more, and then, the filtered solution was vacuum dried to obtain a compound of tert-Bu-O—(CH$_2$)$_6$SiMeCl$_2$ (yield 92%).

In a reactor of −20° C., fluorene (3.33 g, 20 mmol), hexane (100 ml) and MTBE (methyl tert-butyl ether, 1.2 ml, 10 mmol) were introduced, 8 ml of n-BuLi (2.5 M in Hexane) was slowly added, and the solution was stirred at room temperature for 6 hours. After the stirring was completed, the temperature of the reactor was cooled to −30° C., and the above prepared fluorenyl lithium solution was slowly added to a solution of tert-Bu-O—(CH$_2$)$_6$SiMeCl$_2$ (2.7 g, 10 mmol) in hexane (100 ml) at −30° C. for 1 hour. After stirring at room temperature for 8 hours or more, water was added to extract, followed by evaporation to obtain a compound of (tert-Bu-O—(CH$_2$)$_6$)MeSi(9-C$_{13}$H$_{10}$)$_2$ (5.3 g, yield 100%). The structure of the ligand was confirmed through 1H-NMR.

1H NMR (500 MHz, CDCl3): −0.35 (MeSi, 3H, s), 0.26 (Si—CH2, 2H, m), 0.58 (CH2, 2H, m), 0.95 (CH2, 4H, m), 1.17(tert-BuO, 9H, s), 1.29(CH2, 2H, m), 3.21(tert-BuO-CH2, 2H, t), 4.10(Flu-9H, 2H, s), 7.25(Flu-H, 4H, m), 7.35(Flu-H, 4H, m), 7.40(Flu-H, 4H, m), 7.85(Flu-H, 4H, d).

(2) Preparation of a Transition Metal Compound

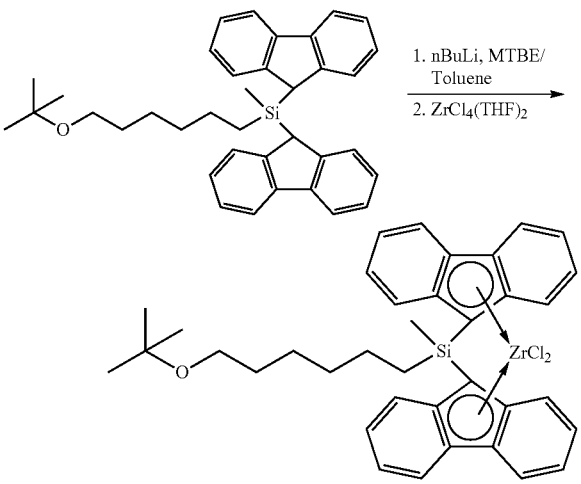

4.8 ml of n-BuLi (2.5 M in Hexane) was slowly added to a solution of (tert-Bu-O—(CH$_2$)$_6$)MeSi(9-C$_{13}$H$_{10}$)$_2$ (3.18 g, 6 mmol)/MTBE (20 ml) at −20° C., and the solution was reacted for 8 hours or more while raising the temperature to room temperature, and then, the above prepared slurry solution of dilithium salts was slowly added to a slurry solution of ZrCl$_4$(THF)$_2$ (2.26 g, 6 mmol)/hexane (20 ml) at −20° C., and the solution was further reacted at room temperature for 8 hours. The precipitate was filtered and washed with hexane several times to obtain a compound of (tert-Bu-O—(CH$_2$)$_6$)MeSi(9-C$_{20}$H$_{14}$)$_2$ZrCl$_2$ in the form of red solid (4.3 g, yield 94.5%).

1H NMR (500 MHz, C$_6$D$_6$): 1.15(tert-BuO, 9H, s), 1.26 (MeSi, 3H, s), 1.58 (Si—CH2, 2H, m), 1.66 (CH2, 4H, m), 1.91(CH2, 4H, m), 3.32(tert-BuO-CH2, 2H, t), 6.86 (Flu-H, 2H, t), 6.90 (Flu-H, 2H, t), 7.15 (Flu-H, 4H, m), 7.60 (Flu-H, 4H, dd), 7.64(Flu-H, 2H, d), 7.77(Flu-H, 2H, d)

EXAMPLE 1

Synthesis of Polyolefin (1) Preparation of a Transition Metal Catalyst Composition The transition metal compound of Preparation Example 1 ((tert-Bu-O—(CH$_2$)$_6$)MeSi(9-C$_{19}$H$_{15}$)$_2$ZrCl$_2$) and a cocatalyst of methylaluminoxane were mixed in a toluene solvent at a ratio of Al/Zr=3,000 to prepare a transition metal catalyst composition.

(2) Synthesis of Olefin Polymer 5 ml of 1-hexene was introduced into the above obtained transition metal catalyst composition under a pressure of 3.5 bar, and while introducing ethylene for 30 minutes, a copolymerization reaction was progressed at a temperature of 90° C., and the results were measured and shown in Table 1.

EXAMPLE 2

Preparation of Polyolefin

Polyolefin was prepared by the same method as Example 1, except that the compound of Preparation Example 2 ((tert-Bu-O—(CH$_2$)$_6$)MeSi(9-C$_{20}$H$_{14}$)$_2$ZrCl$_2$) was introduced instead of the compound of Preparation Example 1 ((tert-Bu-O—(CH$_2$)$_6$)MeSi(9-C$_{19}$H$_{15}$)$_2$ZrCl$_2$), and the results were measured and shown in Table 1.

COMPARATIVE EXAMPLE 1

Preparation of Polyolefin

Polyolefin was prepared by the same method as Example 1, except that the compound of Preparation Example 3 ((tert-Bu-O—(CH$_2$)$_6$)MeSi(9-C$_{13}$H$_9$)$_2$ZrCl$_2$) was introduced in the reactor instead of the compound of Preparation Example 1 ((tert-Bu-O—(CH$_2$)$_6$)MeSi(9-C$_{19}$H$_{15}$)$_2$ZrCl$_2$), and the results were measured and shown in Table 1.

EXAMPLE 3

Preparation of Polyolefin (1) Preparation of a Transition Metal Catalyst Composition The transition metal compound of Preparation Example 1 ((tert-Bu-O—(CH$_2$)$_6$)MeSi(9-C$_{19}$H$_{15}$)$_2$ZrCl$_2$) and a cocatalyst of methylaluminoxane were mixed in a hexane solvent at a ratio of Al/Zr=100 to prepare a transition metal catalyst composition.

(2) Synthesis of Olefin Polymer

To above obtained transition metal catalyst composition was supported in alumina to prepare a supported catalyst, into which 100 ml of 1-hexene was introduced under a pressure of 40 bar, and while introducing ethylene for 1 hour, a copolymerization reaction was progressed at a temperature of 80° C., and the results were measured and shown in Table 1.

EXAMPLE 4

Preparation of Polyolefin

Polyolefin was prepared by the same method as Example 3, except that the compound prepared in Preparation Example 2 ((tert-Bu-O—(CH$_2$)$_6$)MeSi(9-C$_{20}$H$_{14}$)$_2$ZrCl$_2$) was introduced instead of the compound prepared in Preparation Example 1 ((tert-Bu-O—(CH$_2$)$_6$)MeSi(9-C$_{19}$H$_{15}$)$_2$ZrCl$_2$), and the results were measured and shown in Table 1.

COMPARATIVE EXAMPLE 2

Preparation of Polyolefin

Polyolefin was prepared by the same method as Example 3, except that the compound prepared in Preparation Example 3 tert-Bu-O—(CH$_2$)$_6$)MeSi(9-C$_{13}$H$_9$)$_2$ZrCl$_2$) was introduced in the reactor instead of the compound prepared in Preparation Example 1 ((tert-Bu-O—(CH$_2$)$_6$)MeSi(9-C$_{19}$H$_{15}$)$_2$ZrCl$_2$), and the results were measured and shown in Table 1.

TABLE 1

| | Catalytic activity (ton/mol · hr) | Weight average molecular weight(g/mol) | Polydispersity index | Comonomers(mol %) |
|---|---|---|---|---|
| Example 1 | 7.1 | 159,000 | 2.8 | 11.2 |
| Example 2 | 7.5 | 160,000 | 3.6 | 7.4 |
| Comparative Example 1 | 4.5 | 146,000 | 2.9 | 6.4 |
| Example 3 | 2.9 | 443,000 | 2.2 | 0.7 |
| Example 4 | 3.1 | 440,000 | 2.5 | 0.6 |
| Comparative Example 2 | 2.6 | 384,000 | 2.4 | 0.4 |

As shown in Table 1, in the case of Examples 1 and 2 wherein the transition metal compounds obtained in Preparation Examples 1 and 2 were used and a solution copolymerization was conducted, compared to Comparative Example 1 wherein the transition metal compound obtained in Preparation Example 3 was used, catalytic activities were improved, the weight average molecular weight of the produced polyolefins increased, and the concentration of comonomer 1-hexene in the produced polyolefin also increased.

Also, in the case of Examples 3 and 4 wherein the transition metal compounds obtained in Preparation Examples 1 and 2 were used and a supported copolymerization was conducted, compared to Comparative Example 2 wherein the transition metal compound obtained in Preparation Example 3 was used, catalytic activities were improved, the weight average molecular weight of the produced polyolefins increased, and the concentration of comonomer 1-hexene in the produced polyolefin also increased.

Therefore, it was confirmed that in case the transition metal compounds of Examples are used, high catalytic efficiency and activity may be afforded and polyolefin with highly polymerized comonomer 1-hexene may be synthesized.

What is claimed is:

1. A transition metal compound represented by the following Chemical Formula 1:

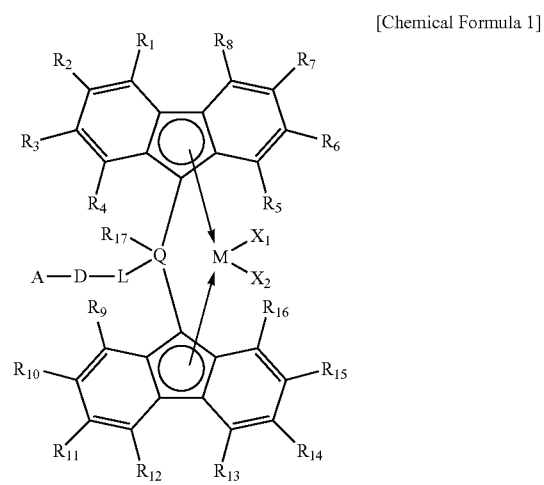

[Chemical Formula 1]

in the Chemical Formula 1,

Q is a Group 14 atom, each of R$_5$, R$_7$, R$_8$, R$_{13}$, R$_{14}$ and R$_{16}$ is independently hydrogen, halogen, a C$_{1-20}$ linear or branched alkyl group, a C$_{2-20}$ linear or branched alkenyl group, a C$_{6-20}$ aryl group, or a C$_{7-20}$ alkylaryl group, at least each of R$_6$ and R$_{15}$ is a functional group of following Chemical Formula 2, R$_1$, R$_2$, R$_3$, R$_4$, R$_9$, R$_{10}$, R$_{11}$ and R$_{12}$ are identical to or different from each other, and are each independently, hydrogen, halogen, a $C_{1-20}$ linear or branched alkyl group, a $C_{2-20}$ linear or branched alkenyl group, a $C_{6-20}$ aryl group, or a $C_{7-20}$ alkylaryl group, $R_{17}$ is a $C_{1-10}$ linear or branched alkyl group, a $C_{2-10}$ linear or branched alkenyl group, a $C_{6-10}$ aryl group, a $C_{7-10}$ alkylaryl group, or a $C_{7-10}$ arylalkyl group, L is a $C_{1-10}$ linear or branched alkylene group, D is —O—, —S—, —N(R)— or —Si(R)(R')—, wherein R and R' are identical to or different from each other, and are each independently, hydrogen, halogen, a $C_{1-20}$ linear or branched alkyl group, a $C_{2-20}$ linear or branched alkenyl group, or a $C_{6-20}$ aryl group, A is hydrogen, halogen, a $C_{1-20}$ linear or branched alkyl group, a $C_{2-20}$ linear or branched alkenyl group, a $C_{6-20}$ aryl group, a $C_{7-20}$ alkylaryl group, a $C_{7-20}$ arylalkyl group, a $C_{1-20}$ alkoxy group, a $C_{2-20}$ alkoxyalkyl group, a $C_{2-20}$ heterocycloalkyl group, or a $C_{5-20}$ heteroaryl group, M is a Group 4 transition metal, $X_1$ and $X_2$ are identical to or different from each other, and are each independently, halogen, a $C_{1-20}$ linear or branched alkyl group, a $C_{2-20}$ linear or branched alkenyl group, a $C_{6-20}$ aryl group, a nitro group, an amino group, a $C_{1-20}$ alkylsilyl group, a $C_{1-20}$ alkoxy group, or a $C_{1-20}$ sulfonate group, and in the above Chemical Formula, →denotes a coordinate bond, -$E_1$-$G_1$      [Chemical Formula 2]

in the Chemical Formula 2, $E_1$ is a $C_{1-10}$ linear or branched alkylene group, and $G_1$ is a $C_{6-20}$ aryl group, a $C_{4-20}$ cycloalkyl group, or a $C_{2-20}$ alkoxyalkyl group.

2. The transition metal compound according to claim 1, wherein $G_1$ is a $C_{6-14}$ aryl group, a $C_{4-10}$ cycloalkyl group, or a $C_{2-15}$ alkoxyalkyl group.

3. The transition metal compound according to claim 1, wherein $G_1$ is a $C_{6-10}$ aryl group or a $C_{5-6}$ cycloalkyl group.

4. The transition metal compound according to claim 1, wherein each of $R_5$, $R_7$, $R_8$, $R_{13}$, $R_{14}$ and $R_{16}$ is hydrogen, halogen, a $C_{1-3}$ linear or branched alkyl group, and each of $R_6$ and $R_{15}$ is a functional group of the following Chemical Formula 3:

-$E_2$-$G_2$      [Chemical Formula 3]

in the Chemical Formula 3, $G_2$ is a $C_{6-10}$ aryl group or a $C_{5-6}$ cycloalkyl group, and $E_2$ is a $C_{1-4}$ linear or branched alkylene group.

5. The transition metal compound according to claim 1, wherein $R_{17}$ is a $C_{1-3}$ alkyl group.

6. The transition metal compound according to claim 1, wherein L is a $C_{3-8}$ linear or branched alkylene group, D is —O— or —S—, and A is a $C_{3-5}$ linear or branched alkyl group.

7. The transition metal compound according to claim 1, wherein each of $R_1$, $R_2$, $R_3$, $R_4$, $R_9$, $R_{10}$, $R_{11}$ and $R_{12}$ of the Chemical Formula 1 is independently hydrogen, halogen or a $C_{1-8}$ linear or branched alkyl group.

8. The transition metal compound according to claim 1, wherein the transition metal compound includes a transition metal compound of the following Chemical Formula 4,

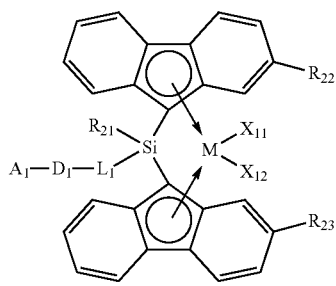

[Chemical Formula 4]

in the Chemical Formula 4,

M is titanium, zirconium, or halfnium, each of $X_{11}$ and $X_{12}$ is halogen, a $C_{1-4}$ linear or branched alkyl group, or a $C_{1-4}$ alkoxy group, $R_{21}$ is a $C_{1-3}$ alkyl group, $L_1$ is a $C_{3-8}$ linear or branched alkylene group, $D_1$ is —O— or —S—, $A_1$ is a $C_{3-5}$ linear or branched alkyl group, each of $R_{22}$ and $R_{23}$ is a functional group of the following Chemical Formula 3, -$E_2$-$G_2$      [Chemical Formula 3]

in the Chemical Formula 3, $G_2$ is a $C_{6-10}$ aryl group or a $C_{5-6}$ cycloalkyl group, and $E_2$ is a $C_{1-4}$ linear or branched alkylene group.

9. A transition metal catalyst composition comprising the transition metal compound of claim 1.

10. The transition metal catalyst composition according to claim 9, wherein the transition metal catalyst composition is used for the synthesis reaction of ethylene/alpha-olefin copolymer.

11. The transition metal catalyst composition according to claim 9, further comprising a cocatalyst.

12. The transition metal catalyst composition according to claim 11, wherein the cocatalyst comprises one or more selected from the group consisting of the compounds of the following Chemical Formula 11, Chemical Formula 12 and Chemical Formula 13:

[L-H]⁺[Z(E)₄]⁻ or [L]⁺[Z(E)₄]⁻      [Chemical Formula 11]

in the Chemical Formula 11,

L is neutral or cationic Lewis base,

[L-H]+ or [L]⁺ is Bronsted acid,

H is a hydrogen atom,

Z is a Group 13 atom, and

Es are identical to or different from each other, and are each independently, halogen having hydrogen valence of one or more, a $C_{1-20}$ hydrocarbyl, a $C_{6-20}$ aryl group or a $C_{1-20}$ alkyl group substituted or unsubstituted with an alkoxy or phenoxy functional group, D(R₃₁)₃      [Chemical Formula 12]

in the Chemical Formula 12,

D is aluminum or boron, $R_{31}$s are identical to or different from each other, and are each independently, halogen; a $C_{1-20}$ hydrocarbon group; or a $C_{1-20}$ hydrocarbon group substituted with halogen,

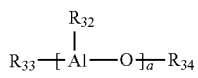

[Chemical Formula 13]

in the Chemical Formula 13, $R_{32}$, $R_{33}$ and $R_{34}$ are identical to or different from each other, and are each independently, hydrogen; a halogen group; a $C_{1-20}$ aliphatic hydrocarbon group; or a $C_{1-20}$ aliphatic hydrocarbon group substituted with halogen, and a is an integer of 2 or more.

13. The transition metal catalyst composition according to claim 12, wherein the mole number of the transition metal compound of the Chemical Formula 1: the mole number of the compound of the Chemical Formula 11 is 1:1 to 1:10.

14. The transition metal catalyst composition according to claim 12, wherein the mole number of the transition metal compound of the Chemical Formula 1: the mole number of the compound of the Chemical Formula 12 or Chemical Formula 13 is 1:1 to 1:8,000.

15. The transition metal catalyst composition according to claim 9, further comprising 50 to 1,000 parts by weight of an organic solvent, based on 100 parts by weight of the transition metal compound.

16. The transition metal catalyst composition according to claim 9, further comprising a carrier in which the active ingredient of a catalyst is fixed.

17. A method of preparing polyolefin, comprising the step of polymerizing olefin monomers in the presence of the transition metal catalyst composition of claim 9.

18. The method of preparing polyolefin according to claim 17, wherein the olefin monomer includes ethylene or alpha-olefin having a carbon number of 3 or more.

19. The method of preparing polyolefin according to claim 17, wherein the polyolefin includes ethylene/alpha-olefin copolymer.

20. The method of preparing polyolefin according to claim 17, wherein the polymerization reaction is progressed at a temperature of 45° C. to 200° C.

21. The transitional metal compound according to claim 1, wherein the transition metal compound includes a transition metal compound selected from:

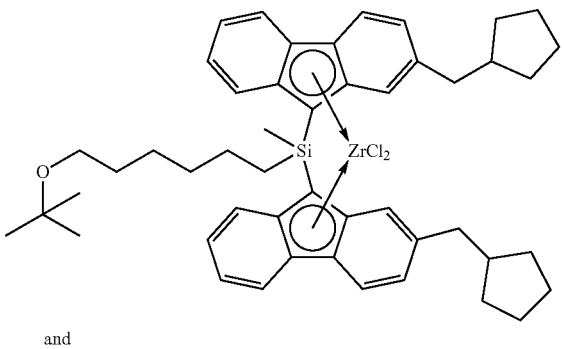

and

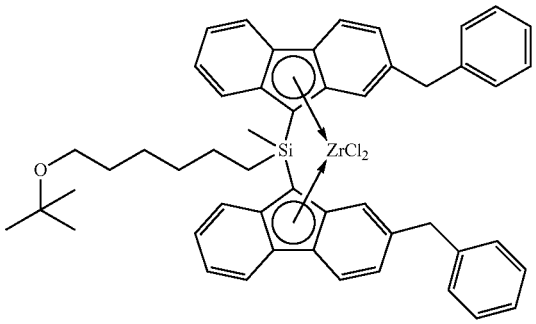

* * * * *